United States Patent [19]
Muller et al.

[11] Patent Number: 5,807,240
[45] Date of Patent: Sep. 15, 1998

[54] CONTINUOUS FLOW ENDOSCOPE WITH ENLARGED OUTFLOW CHANNEL

[75] Inventors: Richard P. Muller, Bronx, N.Y.; James A. Howland, Stamford, Conn.

[73] Assignee: Circon Corporation, Goleta, Calif.

[21] Appl. No.: 719,156

[22] Filed: Sep. 24, 1996

[51] Int. Cl.$^6$ .................................................. A61B 1/30
[52] U.S. Cl. ......................................... 600/135; 600/105
[58] Field of Search ................................. 600/105, 135, 600/136, 137, 138, 153, 156

[56] References Cited

U.S. PATENT DOCUMENTS

| | | | |
|---|---|---|---|
| 3,835,842 | 9/1974 | Iglesias | 128/7 |
| 3,900,022 | 8/1975 | Widran | 600/105 |
| 3,939,839 | 2/1976 | Curtiss | 600/105 X |
| 4,132,227 | 1/1979 | Ibe | 600/105 |
| 4,423,727 | 1/1984 | Widran et al. | 600/105 X |
| 4,920,961 | 5/1990 | Grossi et al. | 606/14 |
| 5,320,091 | 6/1994 | Grossi et al. | 128/4 |
| 5,392,765 | 2/1995 | Muller | 128/4 |
| 5,486,155 | 1/1996 | Muller et al. | 600/137 |
| 5,509,892 | 4/1996 | Bonnet | 600/135 X |

FOREIGN PATENT DOCUMENTS

| | | | |
|---|---|---|---|
| 405250 | 1/1991 | European Pat. Off. | 600/105 |
| 2637747 | 2/1978 | Germany | 600/105 |

*Primary Examiner*—Beverly M. Flanagan
*Attorney, Agent, or Firm*—Perman & Green, LLP

[57] ABSTRACT

An endoscope with a working element and a sheath assembly. The sheath assembly has an outer sheath with an outer tube, and inner sheath with an inner tube and an insulating tip. An inflow channel is formed inside the inner tube. An outflow channel is formed between the inner and outer tubes. The insulating tip is connected to the front of the inner tube and has two holes; one for inflow and one for outflow. The top side of the inner tube has a flat shape to form an enlarged outflow channel area between the flat top side and the outer tube.

18 Claims, 4 Drawing Sheets

CONTINUOUS FLOW ENDOSCOPE WITH ENLARGED OUTFLOW CHANNEL

BACKGROUND OF THE INVENTION

1. Field of the Invention

The present invention relates to medical endoscopes and, more particularly, to a continuous flow endoscope sheath assembly.

2. Prior Art

U.S. Pat. No. 3,835,842 discloses the Iglesias continuous flow endoscope. U.S. Pat. No. 4,920,961 discloses a latching system for connecting inner and outer sheaths to each other and for connecting the inner sheath to a working element. U.S. Pat. No. 5,486,155 discloses a rotatable continuous flow endoscope sheath. U.S. Pat. No. 5,320,091 discloses a continuous flow hysteroscope. U.S. Pat. No. 5,392,765 discloses a continuous flow cystoscope with a front top inlet.

SUMMARY OF THE INVENTION

In accordance with one embodiment of the present invention, an endoscope is provided comprising a working element and a sheath assembly. The sheath assembly is attached to the working element and includes an outer sheath, an inner sheath with an inner tube, and a distal tip. The distal tip comprises dielectric material, is fixedly attached to a front of the inner tube, and has two channels extending from the front of the tip. A first one of the channels extends into the inner tube. A second one of the channels extends to an exterior side of the inner tube.

In accordance with another embodiment of the present invention, a continuous flow resectoscope is provided having a working element and a sheath assembly removably connected to the working element. The sheath assembly has an outer sheath with an outer tube removably connected to an inner sheath with an inner tube. An outflow channel is formed by the inner and outer tubes inside the outer tube and outside the inner tube. The improvement comprises the outflow channel having a cross sectional shape along a majority of the sheath assembly with a relatively large section and a relatively small section.

In accordance with another embodiment of the present invention, a continuous flow resectoscope is provided having a working element and a sheath assembly removably connected to the working element. The sheath assembly has an outer sheath with an outer tube removably connected to an inner sheath. The improvement comprises the inner sheath having an inner tube with a top side along its length that is shaped differently from all other sides of the inner tube. An insulating tip is connected to a front of the inner tube. The insulating tip has a hole extending from a front of the insulating tip to a location in front of the top side at an exterior of the inner tube.

BRIEF DESCRIPTION OF THE DRAWINGS

The foregoing aspects and other features of the invention are explained in the following description, taken in connection with the accompanying drawings, wherein:

FIG. 1a is an elevational side view of a resectoscope incorporating features of the present invention;

FIG. 1b is a partial enlarged cross-sectional view of the attachment of the sheath assembly to the working element of the resectoscope shown in FIG. 1a;

FIG. 2 is a schematic front elevational view of the resectoscope shown in FIG. 1a;

FIG. 3 is an enlarged perspective view of the front of the resectoscope shown in FIG. 1a;

FIG. 5 is a cross-sectional view of the tip used in the sheath assembly shown in FIG. 1a;

FIG. 6 is a cross-sectional view taken along line 6—6 of FIG. 1a;

DETAILED DESCRIPTION OF THE PREFERRED EMBODIMENTS

Figure 1:
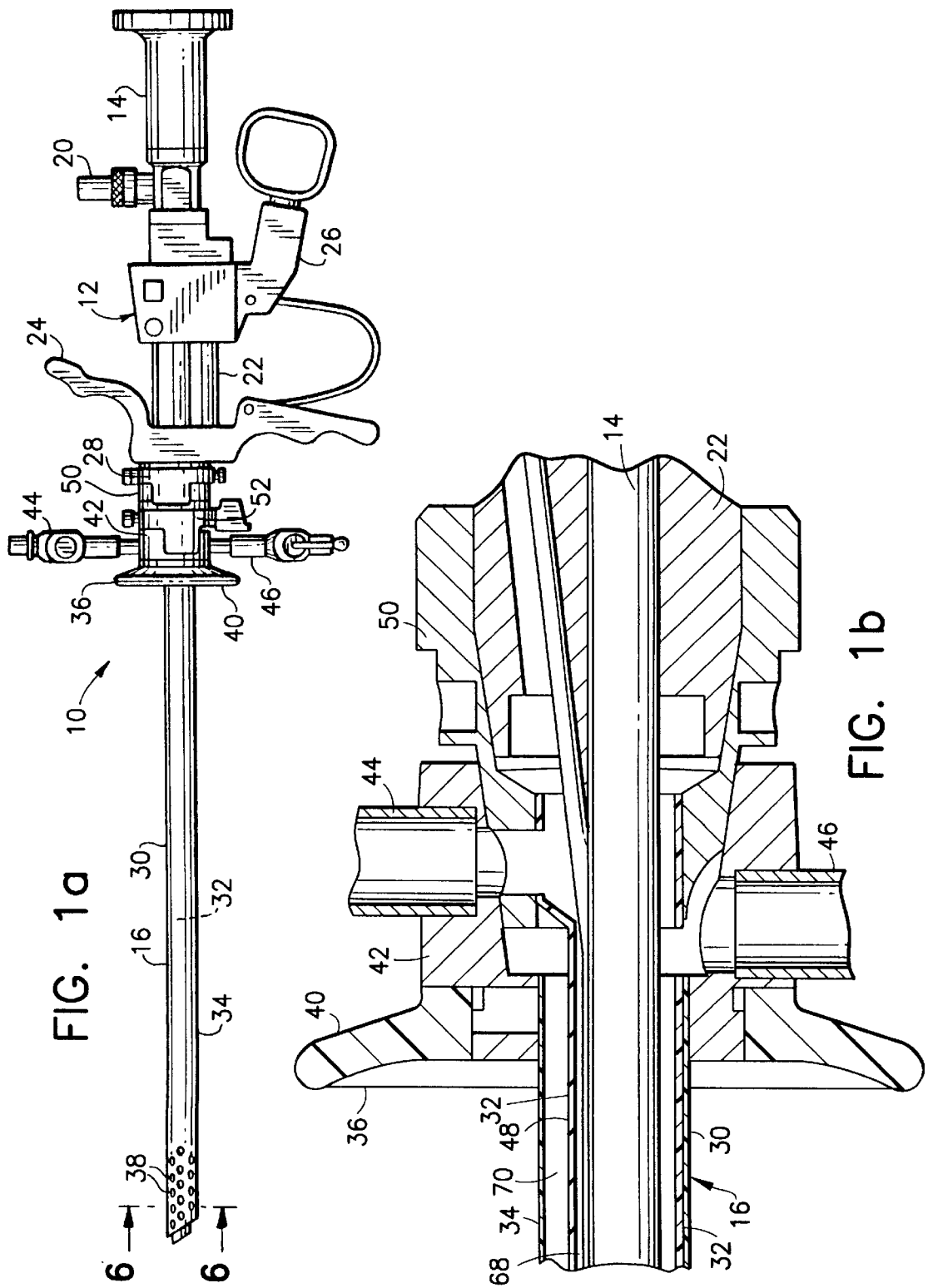

Referring to FIG. 1, there is shown an elevational side view of a resectoscope 10 incorporating features of the present invention. Although the present invention will be described with reference to the embodiments shown in the drawings, features of the present invention can be embodied in various different forms of alternate embodiments and alternate types of endoscopes. In addition, any suitable size, shape or type of elements or materials could be used.

Figure 2:
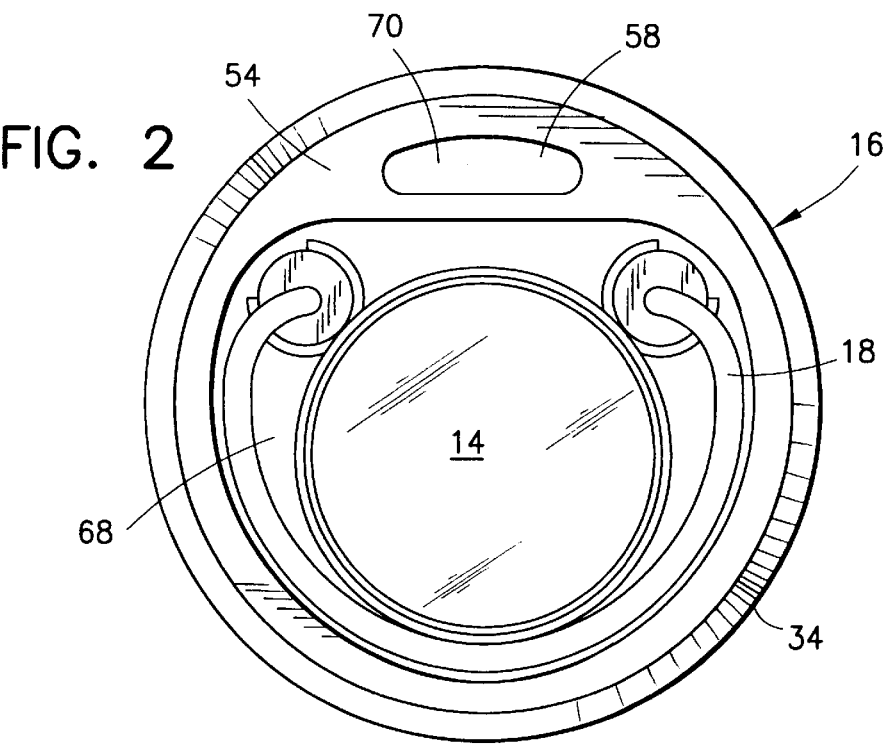

The resectoscope 10 generally comprises a working element 12, a telescope 14, a sheath assembly 16 and a throughput device 18 (see FIG. 2). The throughput device is a tool, such as an electrode or a fiber optic laser guide. The device 18 has a stabilizer 19 (see FIG. 6) that slidingly mounts the device 18 on the telescope 14. The working element 12 and telescope 14, in the embodiment shown, are a U.S.A. ELITE SYSTEM working element and telescope. U.S.A. ELITE SYSTEM is a trademark of Circon Corporation of Goleta, Calif. The telescope 14 is removably mounted to the working element 12, and has a connector 20 for connecting fiber optics in the telescope with a light source by means of a flexible light transmitting cable (not shown). The working element 12 generally comprises a frame 22, a front handle 24, a movable portion 26, and a latch assembly 28. The working element 12, telescope 14 and throughput devices are well known in the art. In alternate embodiments, any suitable type of working element, telescope and/or throughput device could be used.

Referring also to FIG. 1b, the sheath assembly 16 generally comprises an outer sheath 30 and an inner sheath 32. The outer sheath 30 includes an outer tube 34 and a rear end section 36. The outer tube 34 preferably has a circular cross-section. However, in an alternate embodiment, it could have a general oval shape or any other suitable shape. The outer tube 34 has holes 38 in its front end and a substantially uniform outer perimeter. The rear end section 36 is attached to the rear of the outer tube 34. The rear end section 36 has a shield 40, a connector 42, a fluid inlet 44 and a fluid outlet 46. The inner sheath 32 has an inner tube 48, a frame member 50 and a movable latch 52.

Figure 3:
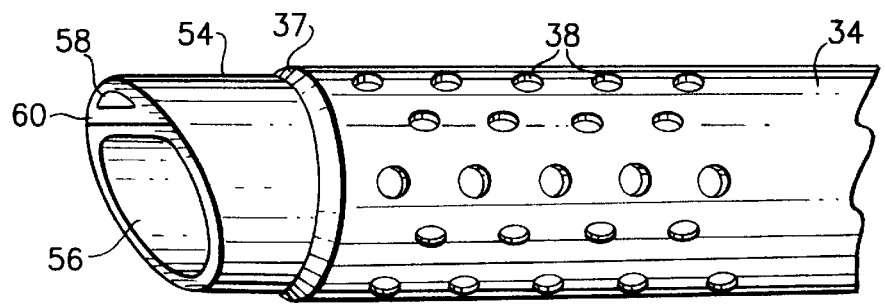

Referring also to FIGS. 2–5, located at the front end 53 of the inner tube 48 is a tip 54. The tip 54 is fixedly attached to the inner tube 48. The tip 54 is preferably made of a dielectric material, such as ceramic or a molded plastic or polymer material. The tip 54 electrically insulates the electrode front of the device 18 from the two tubes 34, 48. In an alternate embodiment, such as when the device 18 is a laser, the tip 54 could be comprised of metal and be an integral feature of the inner sheath tube; not a separate part. As seen best in FIG. 5, the tip 54 has a first main hole 56 and a second hole 58. The first hole 56 extends from the front 60 of the tip 54 to the rear end 61 of the tip. The second hole 58 extends from the front 60 of the tip 54 to an angled top surface 62 at the middle of the tip. The second hole 58 is located at a top of the tip 54. As seen with reference to FIGS. 4 and 5, the front 53 of the inner tube 48 is attached on and around the rear portion 64 of the tip 54. The top 66 of the rear portion 64 is flat. The rest of the outer perimeter of the tip 54 (except at the ends 60, 61 and surface 62) is curved. As seen in FIG. 3, the front 37 of the outer tube 34 fits on the tip 54. In an alternate embodiment, the tip 54 could have a receiving area for the front 37 of the outer tube 34 such that the outer perimeter of the outer tube 34 is flush with the outer perimeter of the tip 54. In other alternate embodiments, any suitable interface of the front of the outer tube with the tip could be provided.

Figure 4:
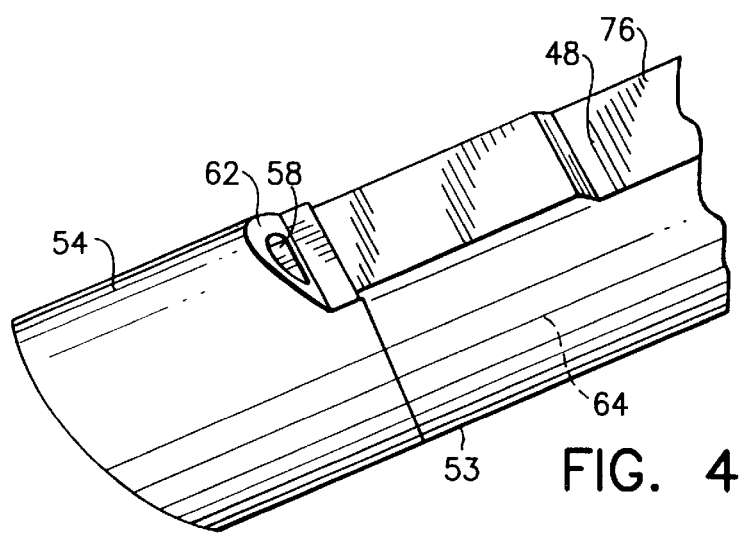
FIG. 4 is an enlarged perspective view of the front of the resectoscope shown in FIG. 1a without the outer sheath.
Figure 5:
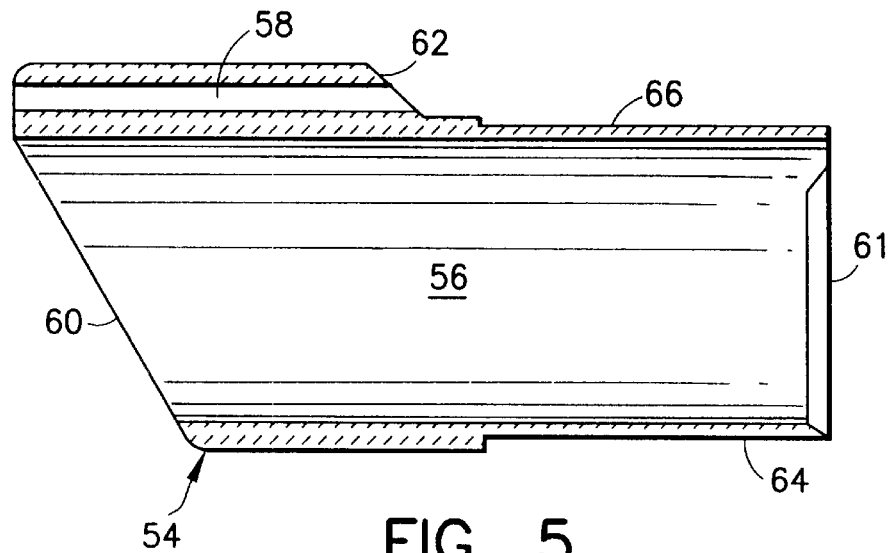
Figure 6:
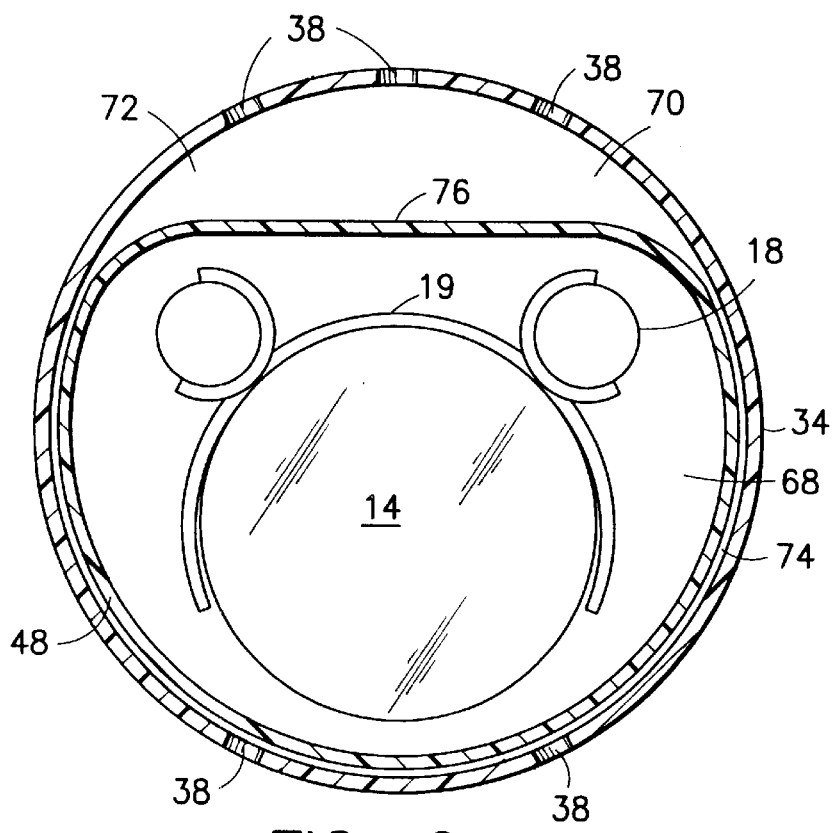

The inner tube 48 and the main hole 56 form an inflow channel 68. The inflow channel 68 forms a path for fluid to pass from the fluid inlet 44 and frame member 50 to the outlet at the front end of the tip 54. The telescope 14 and device 18 also extend through the channel 68. The inner tube 48 and the outer tube 34 form an outflow channel 70. Referring also to FIG. 6, the outflow channel 70 has an enlarged outflow channel area 72 and a relatively smaller outflow channel area 74. The outflow channel 70 has two types of inlets. The hole 58 in the tip 54 forms a forward facing inlet. The holes 38 in the front of the outer tube 34 form lateral facing inlets. The channel 70 extends from the inlets, through the area between the two tubes 48, 34, and out the outlet 46 at the rear end 36 of the outer sheath. As seen in FIGS. 4 and 6, the inner tube 48 is substantially circular in cross-section, but has a relatively flat top side 76. Thus, the inner tube 48 has a general truncated ring shaped cross-section. The outer tube 34 has a general circular cross-section. The area between the top side 76 of the inner tube 48 and the outer tube 34 forms the enlarged outflow channel area 72 along the length of the sheath assembly. The enlarged area 72 is located directly behind the second hole 58 of the tip 54. The enlarged area 72 has a general arch or archway shape. The second relatively smaller area 74 is adjacent the enlarged area 72. The second area 74 surrounds the rest of the inner tube 48. However, in an alternate embodiment, the second area need not be provided. The old resectoscopes provided uniform ring shaped outflow paths. However, the present invention provides an enlarged concentrated area 72 and the smaller area 74. In the embodiment shown, holes 38 in the outer tube 34 extend into both areas 72, 74. However, if the holes 38 become blocked, such as in a narrow passage, the front hole 58 still allows inflow into the outflow channel 70.

Most continuous flow resectoscopes that use electrodes and a telescope having a diameter of about 4 mm have an outer sheath size in the range of about 25 Fr (French) to about 29 Fr. There is always a desire to minimize the size of the outer sheath to reduce trauma and discomfort to the patient. However, the problem with merely trying to reduce the dimensional size of a normal coaxial sheath assembly is that the outflow channel becomes too small to function adequately. With continuous flow endoscopes, the outflow channel must be large enough not to be blocked by debris from electrode cutting or burning. In addition, the outflow channel needs to be cross-sectionally large enough such that surface drag does not prevent the fluid from properly traveling out the outflow channel with a desired flow rate. The present invention, by providing an enlarged outflow channel area 72, allows the size of the outer tube 34 to be reduced to about 22.6 Fr. The present invention provides the cross-section of the inner tube 48 to be more closely tailored to the outer perimeter of the telescope 14 and device 18, while still allowing sufficient open space for inflow of fluid in the inflow channel 68. Thus, the telescope 14 used with the present invention can be the same size as those used in the older and larger resectoscopes. Alternatively, smaller size telescopes could be used with even smaller sheath assemblies. The devices 18 used with the present invention could also be the same as those used in the older and larger resectoscopes or, alternatively, could be even smaller. However, in the embodiment shown, the size of the sheath assembly has only about a 22.6 Fr. outer tube size. The present invention provides this reduced size, but keeps the surface drag sufficiently low to provide an adequate fluid flow rate through the outflow channel. The inner tube could have any suitable cross-sectional shape so long as sufficient area is provided inside the inner tube for the telescope, the device, and inflow of fluid and, so long as sufficient area is provided between the inner and outer tubes for proper outflow of fluid and debris.

Figure 7:
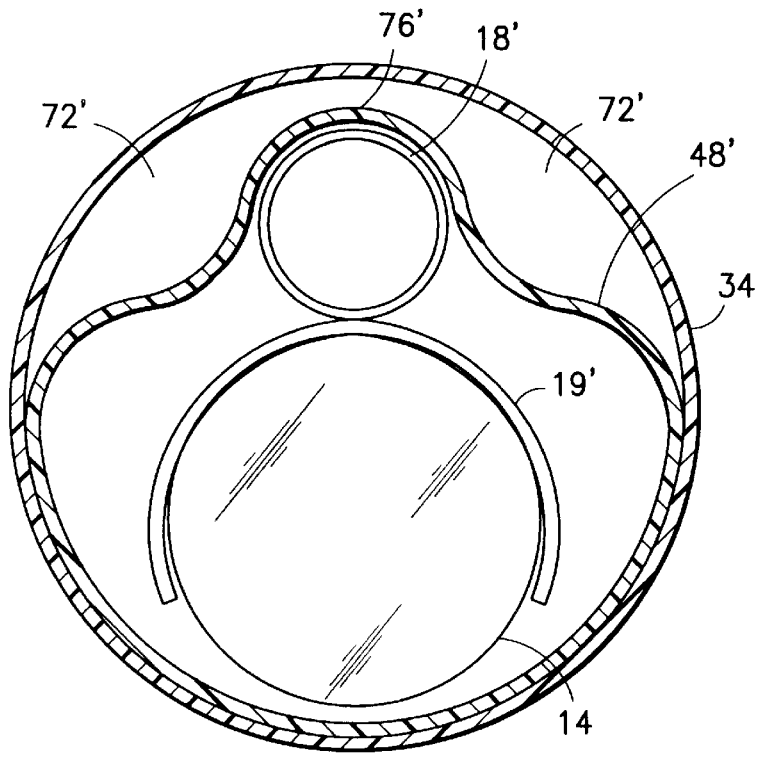
FIG. 7 is a cross-sectional view, similar to that shown in FIG. 6, of an alternate embodiment of the present invention.

Referring now to FIG. 7, a cross-sectional view of an alternate embodiment is shown. In this embodiment, the device 18' is a laser tool and is mounted to the telescope 14 by a stabilizer 19'. The inner tube 48' has a hump-back shaped top side 76'. This forms two enlarged outflow channel areas 72'. This embodiment illustrates once again that the cross-sectional shape of the inner tube can be configured to provide an enlarged outflow channel area while keeping the inflow channel sufficiently large to accommodate the telescope, the device, and to provide an adequate fluid inflow flow rate.

Figure 8:
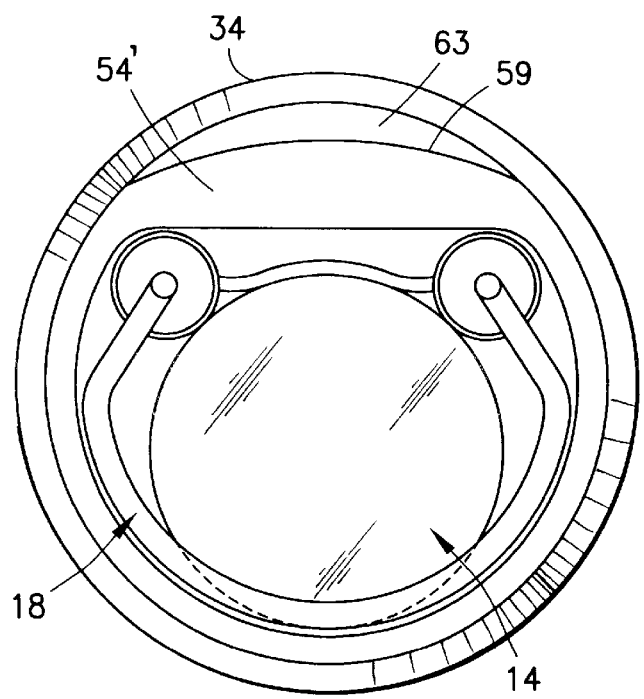
FIG. 8 is a cross-sectional view of another alternate embodiment of the present invention.

Referring now to FIG. 8, a front elevational view of another alternate embodiment is shown. In this embodiment, the tip 54' does not have a second hole. Instead, the tip 54' has a reduced size top side 59 to form an outflow port 63 between the top of the tip 54' and the front of the outer tube 34. In alternate embodiments, other shapes of tips could be provided. In addition, features of the present invention could be incorporated into any suitable type of endoscope. The invention is not limited merely to resectoscopes. In another alternate embodiment, the tip need not be provided with a second outflow hole. Thus, only the holes 38 (see FIG. 3) in the outer tube would be used for the outflow holes. The tip could also have more than two inflow/outflow holes.

It should be understood that the foregoing description is only illustrative of the invention. Various alternatives and modifications can be devised by those skilled in the art without departing from the spirit of the invention. Accordingly, the present invention is intended to embrace all such alternatives, modifications and variances which fall within the scope of the appended claims.

What is claimed is:

1. An endoscope comprising:

a working element; and a sheath assembly attached to the working element, the sheath assembly having an outer sheath, an inner sheath with an inner tube, and a distal tip, wherein the distal tip comprises dielectric material, is fixedly attached to a front of the inner tube, and has two channels extending through the tip from a front end of the tip, a first one of the channels extending from the front end of the tip to a rear end of the tip and into the inner tube and a second one of the channels extending from the front end of the tip to an exterior side of the tip and to an exterior side of the inner tube.

2. An endoscope as in claim 1 wherein the inner tube has a side along its length with a relatively flat shape.

3. An endoscope as in claim 2 wherein an area between the side of the inner tube and the outer sheath forms an enlarged outflow channel area along the length of the inner tube directly behind the second channel of the distal tip.

4. An endoscope as in claim 3 wherein the outer sheath has holes therethrough at a front end of the outer sheath that open into the enlarged outflow channel area.

5. An endoscope as in claim 4 wherein the inner tube and the outer sheath form a relatively smaller outflow channel area that cross-sectionally surrounds the rest of the inner tube adjacent the enlarged outflow channel area.

6. An endoscope as in claim 1 wherein the inner tube has a side along its length with a non-uniform shape to form an enlarged outflow channel area between the inner tube and the outer sheath.

7. An endoscope as in claim 1 wherein the inner tube has a general truncated ring shaped cross-section.

8. An endoscope as in claim 1 wherein the inner tube has a side along its length with a non-flat shape that is spaced a further distance from the outer sheath than the rest of the inner tube to form an enlarged outflow channel area between the inner tube and the outer sheath.

9. In a continuous flow resectoscope having a working element and a sheath assembly removably connected to the working element, the sheath assembly having an outer sheath with an outer tube removably connected to an inner sheath with an inner tube, an outflow channel being formed by the inner and outer tubes inside the outer tube and outside the inner tube, wherein the improvement comprises:

the outflow channel having a cross-sectional shape along a majority of the sheath assembly with a relatively large concentrated section wherein the inner tube has a tip at its front end, the tip having a first channel extending into the inner tube and a side section with a second channel, the tip providing the first and second channels separate and isolated from each other independently from the rest of the sheath assembly, and wherein the second channel extends directly into the outflow channel at a front of the relatively large concentrated section.

10. A resectoscope as in claim 9 wherein the relatively large concentrated section forms a general archway shaped passage.

11. A resectoscope as in claim 9 wherein the outflow channel has a relatively small section to form a general truncated ring shape.

12. A resectoscope as in claim 9 wherein the tip comprises an insulating tip connected to the front end of the inner tube, the insulating tip having the first channel extending into the inner tube and the second channel extending to a location in front of the relatively large section.

13. A resectoscope as in claim 12 wherein the outer tube has holes in its front end that extend into the outflow channel.

14. In a continuous flow resectoscope having a working element and a sheath assembly removably connected to the working element, the sheath assembly having an outer sheath with an outer tube removably connected to an inner sheath, wherein the improvement comprises:

the inner sheath having an inner tube with a top side along its length that is shaped differently from all other sides of the inner tube and an insulating tip connected to a front of the inner tube, the insulating tip having a hole extending from a front end of the insulating tip to a lateral side of the tip at a location in front of the top side at an exterior of the inner tube, wherein the outer sheath surrounds the insulating tip in a rearward direction starting from a location in front of a rear end of the hole.

15. A resectoscope as in claim 14 wherein the top side has a relatively flat shape.

16. A resectoscope as in claim 14 wherein the enlarged outflow channel area extends behind the insulating tip between the top side of the inner tube and the outer tube.

17. A resectoscope as in claim 16 wherein the sheath assembly has a relatively small outflow channel area around the other sides of the inner tube between the inner and outer tubes.

18. A resectoscope as in claim 17 wherein the outer tube has holes in its front end which extend into both the enlarged outflow channel area and the relatively small outflow channel area.

* * * * *